(12) United States Patent
Mole

(10) Patent No.: US 7,763,206 B2
(45) Date of Patent: Jul. 27, 2010

(54) AIR DECONTAMINATION METHOD

(75) Inventor: Alan Mole, Pershore (GB)

(73) Assignee: Tri-Air Developments Limited, London (GB)

( * ) Notice: Subject to any disclaimer, the term of this patent is extended or adjusted under 35 U.S.C. 154(b) by 86 days.

(21) Appl. No.: 11/570,949

(22) PCT Filed: Jun. 29, 2005

(86) PCT No.: PCT/GB2005/002531
§ 371 (c)(1), (2), (4) Date: May 1, 2007

(87) PCT Pub. No.: WO2006/003382
PCT Pub. Date: Jan. 12, 2006

(65) Prior Publication Data
US 2008/0193326 A1    Aug. 14, 2008

(30) Foreign Application Priority Data
Jun. 30, 2004   (GB) ................................. 0414602.3

(51) Int. Cl.
*A61L 9/00* (2006.01)
*A62B 7/08* (2006.01)

(52) U.S. Cl. ............................ 422/4; 422/5; 422/120; 422/121; 422/122; 422/123

(58) Field of Classification Search ....................... None
See application file for complete search history.

(56) References Cited
U.S. PATENT DOCUMENTS 4,244,712 A * 1/1981 Tongret ......................... 96/25
5,891,402 A * 4/1999 Sassa et al. ................. 422/171
2002/0153241 A1 * 10/2002 Niv et al. ..................... 204/164

(Continued)

FOREIGN PATENT DOCUMENTS

EP          0529937          3/1993

(Continued)

OTHER PUBLICATIONS

English machine translation of JP 2000-237529.*

(Continued)

*Primary Examiner*—Elizabeth L. McKane
*Assistant Examiner*—Regina Yoo
(74) *Attorney, Agent, or Firm*—Martin Fleit; Paul D. Bianco; Fleit Gibbons Gutman Bongini & Bianco PL

(57) ABSTRACT

An air decontamination device comprising an air stream generator (20), a non-thermal plasma filter (22), an ultraviolet (UV) radiation emitting device (24), an ozone catalysing device (26), and a hydrocarbon emitter (28). The air stream generator (20) generates and directs an air stream through or across the non-thermal plasma filter (22), the UV radiation emitting device (24), the ozone catalysing device (26), and the hydrocarbon emitter (28). The plasma filter (22) produces free radicals by which contaminants in the air stream are nuetralised. The UV radiation emitting device (24) breaks down ozone in the air stream, catalysed by the ozone catalysing device (26). The hydrocarbon emitter (28) discharges an aromatic hydrocarbon into the air stream to preferentially react with residual ozone so that the air stream becomes suitable for human exposure. A method is also provided.

14 Claims, 1 Drawing Sheet

U.S. PATENT DOCUMENTS

| | | | |
|---|---|---|---|
| 2002/0175068 A1* | 11/2002 | Hammerstrom et al. | 204/164 |
| 2003/0192562 A1* | 10/2003 | Higashi et al. | 131/365 |
| 2004/0140194 A1* | 7/2004 | Taylor et al. | 204/164 |
| 2005/0129591 A1* | 6/2005 | Wei et al. | 422/186 |

FOREIGN PATENT DOCUMENTS

| | | |
|---|---|---|
| EP | 1175916 | 1/2002 |
| GB | 1278043 | 6/1972 |
| JP | 63270547 | 11/1988 |
| JP | 63305922 | 12/1988 |
| JP | 5042231 | 2/1993 |
| JP | 11221489 | 8/1999 |
| JP | 11276563 | 10/1999 |
| JP | 2000140578 | 5/2000 |
| JP | 2000237529 | 9/2000 |
| JP | 2000237529 | 5/2001 |
| JP | 2002263181 | 9/2002 |
| JP | 2002357341 | 12/2002 |
| JP | 2004160363 | 6/2004 |
| WO | WO 00/74820 | 12/2000 |
| WO | WO 03/028880 | 4/2003 |

OTHER PUBLICATIONS

International Prelim. Report on Patentability published Jan. 9, 2007 for PCT/GB05/002531 filed Jun. 29, 2005.

International Search Report published Jan. 12, 2006 for PCT/GB05/002531 filed Jun. 29, 2005.

Written Opinion published Dec. 31, 2006 for PCT/GB05/002531 filed Jun. 29, 2005.

An evaluation of a novel air disinfection system against aerosols of MS2 coliphage, pp. 1-12, Laura O'Donoghue, Issue Date Jun. 8, 2006, HPA Report 40/06.

An evaluation of Tri-Air Developments Plasmalyser Air Purification technology against aerosols of *Bacillus atrophaeus* and *Staphylococcus epidermidis,* pp. 1-16, Sara Speight, Issue Date Sep. 24, 2007, HPA Report 50/07.

An evaluation of Tri-Air Developments Plasmalyser Air Purification technology against surface contamination of MRSA . . . , pp. 1-9, T. Pottage, Issued Sep. 24, 2007, HPA REP 63/07.

Tri-Air Developments test report; Ozone & Indoor Air Quality Test, Jan. 15, 2008, tri-airdevelopmentsltd.

http://www.ars.usda.gov/research/projects/projects.htm?ACCN_NO=409114&fy=2006, Aug. 7, 2008, Research Project:Decontamination of Fresh Product With Cold Plasma.

http://www.sharpusa.com/products/ModelLanding/0,1058,1827,00.html, pp. 1-3, Dec. 22, 2008, Sharp FP-P60CX.

http://www.envirocair.co.uk/envirocair.htm, pp. 1-2, Aug. 7, 2008, Envirocair From Biotech International Ltd.

http://bioquell.co.uk/News.asp?id=41, Eradication of persistent MRSA using hydrogen peroxide vapour (HPV), pp. 1-3, Aug. 7, 2008, BIOQUELL.

http://www.radical.gb.com/TECH-Radical-alternative-to-chlorine.htm, pp. 1-2, Aug. 7, 2008, RADICAL.

British Search Report for GB0414602.3 (priority for this application) dated Oct. 19, 2004.

* cited by examiner

AIR DECONTAMINATION METHOD

FIELD OF THE INVENTION

The present invention relates to a method of decontaminating air, and to a device for use with said method.

BACKGROUND OF THE INVENTION

Air purity and being able to consistently remove contaminants entrained in the air is extremely important, especially in supposedly sterile or hygienic environments, such as hospitals and kitchens. It is also beneficial having decontaminated air in doctors surgeries, and workplace environments making it more difficult for germs and disease to spread.

In addition to microbiological contaminants, chemical gases or vapours can present a serious hazard, either as a by-product of industrial processing or as a malicious attack through terrorism or chemical warfare.

SUMMARY OF THE INVENTION

The present invention seeks to provide a solution to these problems.

According to a first aspect of the present invention, there is provided a method of decontaminating air, the method comprising the steps of:

a) directing an air stream to be decontaminated through a non-thermal plasma filter so that free radicals are produced by which contaminants in the air stream are neutralised;

b) breaking down ozone in the air stream output from the non-thermal plasma filter; and c) introducing an aromatic hydrocarbon into the air stream to preferentially react with residual ozone so that the air stream becomes suitable for human exposure.

Preferable and/or optional features of the first aspect (method) of the invention are set forth below.

According to a second aspect of the present invention, there is provided an air decontamination device for use with a method according to the first aspect of the invention, the device comprising a non-thermal plasma filter, an ultraviolet radiation emitting device, an ozone catalysing device, a hydrocarbon emitter, and an air stream generator by which an air stream can be generated and directed to pass through or across the non-thermal plasma filter, the UV radiation emitting device, the ozone catalysing device and the hydrocarbon emitter.

Preferable and/or optional features of the second aspect (device) of the invention are set forth below.

BRIEF DESCRIPTION OF THE DRAWING

The present invention will now be more particularly described, by way of example, with reference to the accompanying drawing, which shows a diagrammatic cross-sectional side view of an air decontamination device, in accordance with the second aspect of the invention.

Referring to the FIG. 1, there is shown an air decontamination device which comprises a housing 10 having a flow passage 12, an air inlet 14 to the flow passage 12 and an air outlet 16 exiting from the passage 12, and a compartment 18 adjacent the flow passage 12. An air stream generator 20, a non-thermal plasma filter 22, an ultraviolet (UV) radiation emitting device 24, an ozone catalysing device 26, and a hydrocarbon emitter 28 are located in the passage 12.

DETAILED DESCRIPTION OF THE INVENTION

Figure 1:
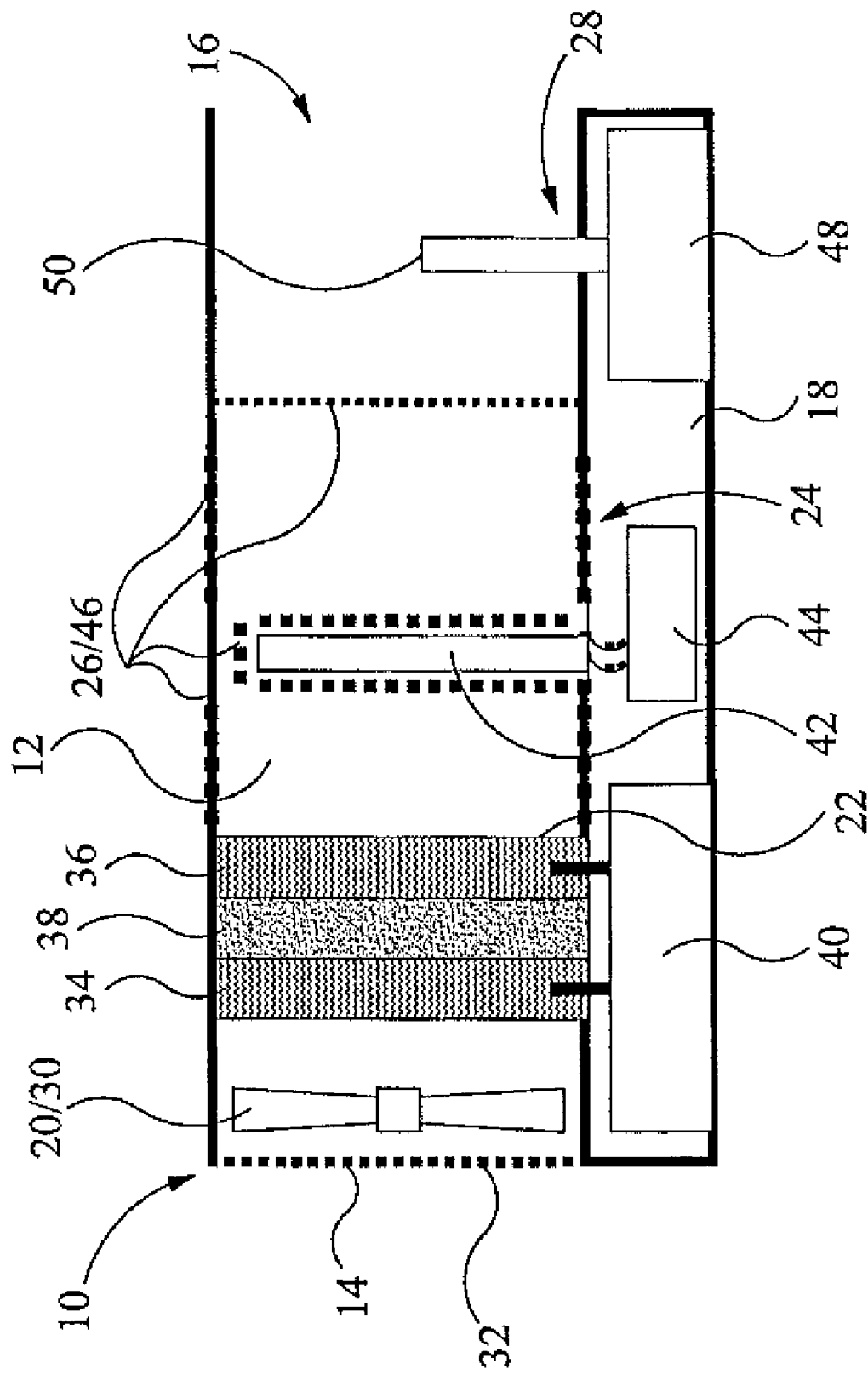

The air stream generator 20 is provided adjacent the air inlet 14 of the passage 12. The air stream generator 20, in this embodiment, is an electric fan 30 powered by mains electricity or battery packs (not shown) provided in the compartment 18 of the housing 10. As a safety measure, a grill 32 is provided across the air inlet 14 to prevent accidental access to the fan 30 while in operation.

The non-thermal plasma filter 22 is positioned adjacent the fan 30, downstream of the air inlet 14. The plasma filter 22 comprises a cathode 34 and anode 36, between which is sandwiched a dielectric 38. The cathode 34 and anode 36 are powered by a power supply unit (PSU) 40 housed in the compartment 18 of the housing 10.

The cathode 34 and anode 36 comprise reticulated (three dimensionally porous) conductive elements, in this case being aluminium and carbon composite. However, any rigid reticulated conductive or semi-conductive material could be used.

The dielectric 38 is activated alumina pellets, nominally 3 to 4 millimeters in diameter. However, again, the dielectric 38 could be any suitable material to suit varying applications and specific requirements. The dielectric 38 material may be coated with a catalytic material.

The UV radiation emitting device 24 includes an ultraviolet light emitting tube 42 powered by a PSU 44 housed in the compartment 18 of the housing 10. The UV light emitting tube 42 is disposed in the passage 12, downstream of the non-thermal plasma filter 22, and coincident with the ozone catalysing device 26.

The ozone catalysing device 26 comprises a mesh 46 disposed across the passage 12 and surrounding the UV light emitting tube 42. The mesh 46 includes a coating of ozone catalysing material, such as a mixture of titanium, lead and manganese oxides.

The hydrocarbon emitter 28 includes a rechargeable hydrocarbon reservoir 48 located in the compartment 18 of the housing 10, an evaporator 50 for evaporating liquid hydrocarbon held in the reservoir 48, and a pump (not shown) by which the gaseous hydrocarbon is discharged into the passage 12. The reservoir 48 contains a liquid aromatic hydrocarbon, for example an olefin such as a Terpene and, more specifically, Myrcene. The outlet 16 of the hydrocarbon emitter 28 is located at or in the vicinity of the centre of the passage 12 of the housing 10, and downstream of the UV light emitting tube 42 and mesh 46 of the ozone catalysing device 26. The outlet 16 of the hydrocarbon emitter 28 is located adjacent the outlet 16 of the passage 12 of the housing 10.

Any other suitable means for supplying volatised aromatic hydrocarbon to the outlet 16 of the hydrocarbon emitter 28 can be used.

The air decontamination device can be solely powered by mains electricity, solely powered by battery packs, which may be rechargeable, or may be selectively energisable by both power sources.

The air decontamination device can be produced in the form of a portable device, and this can take the dimensions of or substantially of a suitcase. Alternatively, the air decontamination device can be produced as a larger device intended to remain in one location once installed. The latter device is more suitable for, but not limited to, industrial or commercial installations and premises.

In use, the air decontamination device is positioned in the location to be decontaminated. The device is intended to decontaminate air within a building, chamber, enclosure, trunking, pipe, channel or other enclosed or substantially enclosed area. However, with sufficient through-flow capacity, it can also decontaminate air in an open outside environment.

The device is energised, and the fan 30 generates a stream of ambient air along the passage 12 of the housing 10. The air stream passes initially through the non-thermal plasma filter 22. The filter utilises the characteristics of a non-thermal plasma to "plasmalise" the constituent parts of the air within the dielectric core. In general terms, the outer ring electrons in the atomic structure of the elements comprising air (principally oxygen and nitrogen) are "excited" by the intense electronic field generated by the non-thermal plasma, typically being 10 Kv at 20 KHz. The energised electrons release energy through collisions. However, little or no heat is emitted due to the insubstantial mass of the electrons and the consequent lack of ionisation that occurs. The released energy is sufficient to generate free radicals within the air stream, such as $O^-$ and $OH^-$. The free radicals are powerful oxidants, and will oxidise hydrocarbons, organic gases, and particles typically 2.5 picometers and below, such as bacteria, viruses, spores, yeast moulds and odours. Only the most inert elements or compounds will generally resist oxidation.

Since many of the resultants of the oxidative reactions are transient and surface acting, due to having zero vapour pressure, by providing a molecular thick catalytic coating on some or all of the dielectric material of the non-thermal plasma, oxidation of particular molecules or compounds, for example nerve gas agents, within the non-thermal plasma can be targeted.

The non-thermal plasma filter 22 produces ozone as one of the by-products. This is entrained in the air stream leaving the non-thermal plasma filter 22. The half-life of ozone is dependent on atmospheric conditions and, itself being a powerful oxidant, under normal circumstances will continue to react in the air long after it has exited the plasma core. This is unacceptable for a device operated by and in the general vicinity of people.

The air stream leaving the non-thermal plasma filter 22 therefore passes to the UV light emitting tube 42 and through the surrounding mesh 46 of the ozone catalysing device 26. The ultraviolet radiation emitted at 253.4 nanometers wavelength by the UV light emitting tube 42 acts to break down the ozone entrained in the air stream leaving the plasma filter 22. The coating on the mesh 46 acts to catalyse this break down.

This destruction (photo-oxidation) of the ozone increases the free radical level, and particularly the level of Hydroxyl radicals $OH^-$, within the air stream. These free radicals also vigorously oxidise contaminants remaining within the air stream.

Trials have shown that free radicals resident in the air stream post-plasma filtering significantly increase the rate of generation of free radicals during the photo-oxidative process.

It is not possible to destroy all of the ozone entrained in the air stream from the plasma filter 22 using the UV radiation emitting device 24 and ozone catalysing device 26. Experimentation has shown that an air stream containing 7 parts-per-million (ppm) ozone will still have 10% to 12% of the ozone surviving the process. This potentially results in an ozone concentration in the order of 840 parts-per-billion (ppb), which is around eight times greater than recommended levels for human exposure.

The air stream thus exits the ozone catalysing device 26 and passes along the passage 12 to the hydrocarbon emitter 28. The hydrocarbon emitter 28 discharges volatised aromatic hydrocarbon into the air stream in order to reduce the remaining residual ozone to acceptable levels. Myrcene is suggested, since it is naturally occurring, has no known toxicity, and is widely used to 'extend' perfumes and fragrances.

Myrcene contains three carbon=carbon double bonds in its molecular structure. Ozone reacts preferentially with Myrcene evaporated into the air stream. When Myrcene reacts with ozone, a 'free radical cascade' is triggered. More than thirty interrelated reactions occur, many of which produce a series of short half life oxidants such as hydro peroxides, super oxides, hydro-oxy peroxides, and hydroxy peroxides. Each of these oxidants breaks down releasing yet further free radicals, which in turn promulgate the production of these oxidative species. This process continues until all the residual ozone is utilised.

The products of these preferential reactions have zero vapour pressure, and hence condense on any remaining particle in the air stream or surface. As a result, decontamination of contaminants within the ambient air, once the decontaminated air stream exits through the outlet 16 of the housing 10, occurs.

These initiated condensation reactions outside of the decontamination device may cause small particulate 'growing', resulting, in extreme cases, in a visible fog or mist. This is undesirable. However, due to the air decontamination device effectively recirculating and re-decontaminating air within an environment, these small particulates are in any event removed within the non-thermal plasma filter 22.

The small particulates are actually beneficial in that they fuel the production of hydroxyl radicals within the plasma filter 22 once recirculated. Thus, although the potential for a visible fog is undesirable, it is beneficial in increasing the efficiency of the decontamination device, and thus the resultant safety of the ambient air.

The air stream generator can be driven in reverse, enabling decontamination of the interior of the device by drawing excess free radicals entrained in the air stream back through the device. As such, the device is largely self-cleaning.

The embodiment described above is given by way of example only, and modifications will be apparent to persons skilled in the art without departing from the scope of the invention as defined by the appended claims.

The invention claimed is:

1. A method of decontaminating air using a continual supply of free radicals, the method comprising the steps of:
   (a) first, directing an air stream to be decontaminated through a device including a non-thermal plasma filter whereby free radicals are produced by which contaminants in the air stream are neutralized;
   (b) second, breaking down ozone in the air stream output from the non-thermal plasma filter by subjecting the air stream to ultra-violet radiation in the presence of a catalyst to increase free-radical level;
   (c) third, introducing a hydrocarbon having a carbon-carbon double bond into the air stream to preferentially react with residual ozone initiating a free radical cascade which continues outside of the device forming particulates in ambient air; and
   (d) fourth, re-circulating an air stream containing the particulates from the ambient air through the device including the non-thermal plasma filter wherein the particulates increase efficiency of production of free radicals.

2. The method of claim 1, wherein the catalyst is a mixture of titanium, lead, and manganese oxides.

3. The method of claim 1, wherein the hydrocarbon is an olefin.

4. The method of claim 3, wherein the olefin is a Terpene.

5. The method of claim 4, wherein the Terpene is Myrcene.

6. The method of claim 1, wherein the hydrocarbon is evaporated into the air stream.

7. The method of claim 1, wherein continuation of the free radical cascade outside of the device provides decontamination of ambient air outside of the device.

8. A method of decontaminating air using a continual supply of free radicals, the method comprising the steps of:
   (a) first, directing an air stream to be decontaminated through a device including a non-thermal plasma filter comprising a cathode, an anode, and a dielectric element, whereby free radicals are produced by which contaminants in the air stream are neutralized;
   (b) second, breaking down ozone in the air stream output from the non-thermal plasma filter by subjecting the air stream to ultra-violet radiation in the presence of a catalyst to increase free-radical level;
   (c) third, introducing a hydrocarbon having a carbon-carbon double bond into the air stream to preferentially react with residual ozone initiating a free radical cascade which continues outside of the device forming particulates in ambient air; and
   (d) fourth, re-circulating an air stream containing the particulates from the ambient air through the device including the non-thermal plasma filter wherein the particulates increase efficiency of production of free radicals.

9. The method of claim 8, wherein the catalyst is a mixture of titanium, lead, and manganese oxides.

10. The method of claim 8, wherein the hydrocarbon is an olefin.

11. The method of claim 10, wherein the olefin is a Terpene.

12. The method of claim 11, wherein the Terpene is Myrcene.

13. The method of claim 8, wherein the hydrocarbon is evaporated into the air stream.

14. The method of claim 8, wherein continuation of the free radical cascade outside of the device provides decontamination of ambient air outside of the device.

* * * * *